(12) United States Patent
Lichtenberger

(10) Patent No.: US 6,943,155 B2
(45) Date of Patent: Sep. 13, 2005

(54) UNIQUE COMPOSITIONS OF ZWITTERIONIC PHOSPHOLIPIDS AND BISPHOSPHONATES AND USE OF THE COMPOSITIONS AS BISPHOSPHATE DELIVERY SYSTEMS WITH REDUCED GI TOXICITY

(76) Inventor: Lenard M. Lichtenberger, 5427 Darnell, Houston, TX (US) 77096

( * ) Notice: Subject to any disclaimer, the term of this patent is extended or adjusted under 35 U.S.C. 154(b) by 0 days.

(21) Appl. No.: 09/827,493

(22) Filed: Apr. 6, 2001

(65) Prior Publication Data
US 2002/0022603 A1 Feb. 21, 2002

Related U.S. Application Data
(60) Provisional application No. 60/195,562, filed on Apr. 7, 2000.

(51) Int. Cl.[7] .............................................. A61K 31/66
(52) U.S. Cl. ...................... 514/141; 514/142; 514/143
(58) Field of Search ................................ 514/141, 142

(56) References Cited

U.S. PATENT DOCUMENTS

| | | | |
|---|---|---|---|
| 4,918,063 A | 4/1990 | Lichtenberger | 514/78 |
| 4,950,656 A | 8/1990 | Lichtenberger | 514/78 |
| 5,032,585 A | 7/1991 | Lichtenberger | 514/78 |
| 5,043,329 A | 8/1991 | Lichtenberger | 514/78 |
| 5,134,129 A | 7/1992 | Lichtenberger | 514/78 |
| 5,260,284 A | 11/1993 | Lichtenberger | 514/78 |
| 5,260,287 A | 11/1993 | Barreto et al. | 514/103 |
| 5,763,422 A | 6/1998 | Lichtenberger et al. | 514/78 |
| 5,869,471 A * | 2/1999 | Hovancik et al. | |
| 5,955,451 A | 9/1999 | Lichtenberger et al. | 514/78 |

FOREIGN PATENT DOCUMENTS

| | | | |
|---|---|---|---|
| WO | WO 9904773 | * | 2/1999 |
| WO | WO 00 61111 A | | 10/2000 |

OTHER PUBLICATIONS

International Journal of Pharmaceutics. vol. 162, No. 1–2, 1998, pp. 51–58, XP001064839; N. Van Rooijen, A. Sanders: " Manipulation of Kupffer cells by liposome encapsulated clodronate and propamidine–synergistic and antagonistic effects of liposomal phospholipids and drugs".

* cited by examiner

Primary Examiner—Shaojia Anna Jiang
(74) Attorney, Agent, or Firm—Robert W. Strozier

(57) ABSTRACT

Compositions and methods for treating osteoporosis using the compositions are disclosed where the compositions have reduced GI toxicity and improved bio-availability and include a bisphosphonate and zwitterionic phospholipid.

35 Claims, 9 Drawing Sheets

Alendronate

Risedronate

Pamidronate

Phosphatidylcholine

Alendronate

Risedronate

Pamidronate

Phosphatidylcholine

UNIQUE COMPOSITIONS OF ZWITTERIONIC PHOSPHOLIPIDS AND BISPHOSPHONATES AND USE OF THE COMPOSITIONS AS BISPHOSPHATE DELIVERY SYSTEMS WITH REDUCED GI TOXICITY

RELATED APPLICATION

This application claims provisional priority to U.S. Provisional Application Ser. No. 60/195,562 filed 7 Apr. 2000.

BACKGROUND OF THE INVENTION

1. Field of the Invention

The present invention relates to compositions including bisphosphonate pharmaceuticals having reduced GI toxicity due to the bisphosphonate pharmaceuticals and enhanced bio-availability of bisphosphonate pharmaceuticals after ingestion with food. The present invention also relates to the compositions to treat osteoporosis, methods for treating osteoporosis and methods for preparing the compositions.

More particularly, the present invention relates to compositions including a bisphosphonate and a zwitterionic phospholipid, where the compositions can be taken with meals, have reduced bisphosphonate GI toxicity and/or side-effects and have improved bisphosphonate bio-availability after ingestion with food. The present invention also relates to the compositions to treat osteoporosis, methods for treating osteoporosis and methods for preparing the compositions.

2. Description of the Related Art

Bisphosphonates represent a class of drugs that have shown very promising therapeutic efficacy in the treatment of a number of diseases associated with abnormally accelerated bone resorption including; osteoporosis, Paget's disease and hypercalcemia of malignancy. See e.g., Fleisch H., *Ann Med,* 29, 55–62 (1997) and Fleisch H.,*Drugs,* 42, 919–944 (1991). As an increasing number of these drugs become available for clinical use in the treatment of the millions of individuals with these skeletal diseases, evidence is becoming available that their chronic usage may be associated with a number of gastrointestinal side-effects, such as diarrhea, abdominal pain and inflammation (e.g. esophagitis and gastritis), erosions and ulceration of the upper gastrointestinal tract. See e.g., Maconi G, Bianchi Porro G., *Am J Gastroenterol,* 90, 1889–1890 (1995); Lufkin E G, Argueta R, Whitaker M D, Cameron A L, Wong V H, Egan K S, O'Fallon W M, Riggs B L, *Osteoporos Int,* 4, 320–322 (1994); De Groen P C, Lubbe D J, Hirsch I J, Daifotis A, Stephenson W, Freedholm D, Pryor-Tillotson S, Seleznick M J, Pinkas H, Wang K K, *N Eng J Med,* 335, 1016–1021 (1996). Women, five or more years past the onset of menopause, who are in an estrogen-deficient state, are particularly prone to developing osteoporosis and are also at greatest risk of developing GI side-effects when placed on chronic bisphosphonate therapy.

It has been estimated that 8–10 million Americans are suffering from osteoporosis and an additional 17–20 million of our populace have low bone mass, placing them at risk for this disease. Women constitute ~80% of this "at risk" population. In many cases, these individuals are also taking non-steroidal anti-inflammatory drugs (NSAIDs) to alleviate the pain and inflammation of arthritic joints, further compounding their risk of developing GI complications. In confirmation with these clinical observations, Graham and associates performed a number of endoscopic studies on healthy subjects taking the bisphosphonate, alendronate, for a period up to 2 weeks at doses recommended for the treatment of Paget's Disease (40 mg) or osteoporosis (10 mg) and reported that 40–60% of the volunteers had observable gastric erosions, while 10–20% developed one or more gastric ulcers. See e.g., Graham D Y, Malaty H M, Goodgame R, *Am J Gastroenterol,* 92, 1322–1325 (1997) and Graham D Y, Malaty H M, *Aliment Pharmacol Ther,* 13, 515–519 (1999). In support of these concerns, Lanza reported that alendronate (Fosamax) administered at both at 10 mg and 40 mg doses significantly retarded the rate of healing of aspirin-induced gastric erosions. See e.g., Lanza F L, *Am J Gastroenterol,* 91, 1916 (1996).

In order to investigate the potential mechanism of GI damage due to bisphosphonates under more controlled experimental conditions, a number of laboratories have developed animal models of this condition. Peter et. al. recently compared the chronic effects of increasing doses of alendronate, risedronate and etidronate administered over a 4 week period in rats and reported that all three bisphosphonates induced a dose-dependent injurious effect on mucosae of the gastric body and antrum. The dose-dependent injurious effects were observed both macroscopically and histologically, along with evidence of submucosal inflammation. See e.g., Peter C P, Kindt M V, Majka J A, *Dig Dis Sci,* 43, 1009–1015 (1998).

Blank et al. developed an acute model of bisphosphonate-induced gastric injury in rats that were intragastrically administered high doses of the bisphosphonates alone or in combination with the NSAID, indomethacin. See e.g., Blank M A, Ems B L, Gibson G W, Myers W R, Berman S K, Phipps R J, Smith P N, *Dig Dis Sci,* 42, 281–288 (1997). In these studies, they demonstrated that although the bisphosphonates or the NSAID induced little or no observable macroscopic gastric lesions over the 4 hr study period, concomitant treatment with two classes of drugs resulted in the development of gastric ulcers, along with evidence of mucosal necrosis and inflammatory infiltration of the submucosa. Using this model, they compared several compounds and concluded, contrary to the findings of Peter et al., that the bisphosphonates with a primary amino group (pamidronate and alendronate) were more irritating to the gastric mucosa than those containing a fixed nitrogenous group (risedronate and NE-97221).

Elliott et. al. also employed this rodent model to demonstrate that in combination with indomethacin, only bisphosphonates administered intragastrically (vs. intraperitoneal administration) induced gastric injury, and in a related experiment demonstrated that alendronate significantly delayed the healing of experimentally induced gastric ulcers in rats. See e.g., Elliott S N, McKnight W, Davies N M, MacNaughton W K, Wallace J L, *Life Sci,* 62, 77–91 (1998). Moreover, many bisphosphonates have low bio-availability requiring patients to routinely ingest large doses of the bisphosphonate to get a desired benefit with concurrent increased risk of GI adverse side effects.

Thus, it would be an advancement in the art to have bisphosphonate formulations that reduce or eliminate the adverse effects of bisphosphonates on the upper GI tract, while allowing the bisphosphonates to be taken with meals and thereby increasing the bio-availability of the bisphosphonate when taken with food.

SUMMARY OF THE INVENTION

The present invention provides a mixture comprising a bisphosphonate in its zwitterionic form and a phospholipid in its zwitterionic form.

The present invention provides a medicinal composition comprising a mixture including of a bisphosphonate in its zwitterionic form and a phospholipid in its zwitterionic form, where the phospholipid is in an amount sufficient to reduce GI toxicity of the bisphosphonate and improve bisphosphonate bio-availability when the composition is taken with meals, and the bisphosphonate is in an amount sufficient to reduce bone resorption and/or increase bone density, particularly when the composition is taken with meals.

The present invention provides a medicinal composition comprising an inert carrier and a mixture including a bisphosphonate in its zwitterionic form and a phospholipid in its zwitterionic form, where the phospholipid is present in an amount sufficient to reduce a GI toxicity of the bisphosphonate and improve bisphosphonate bio-availability particularly when the composition is taken with meals, and the amount of bisphosphonate is sufficient to reduce bone resorption and/or increase bone density, particularly when the composition is taken with meals.

The present invention also provides an ionic associated complex comprising a bisphosphonate in its zwitterionic form and a phospholipid in its zwitterionic form.

The present invention provides a medicinal composition comprising an ionic associated complex including an amount of a bisphosphonate in its zwitterionic form and an amount of a phospholipid in its zwitterionic form, where the amount of the phospholipid is sufficient to reduce a GI toxicity of the bisphosphonate and improve bisphosphonate bio-availability when the composition is taken with meals, and the amount of bisphosphonate is sufficient to reduce bone resorption and/or increase bone density, particularly when the composition is taken with meals.

The present invention provides a medicinal composition comprising an inert carrier and an ionic associated complex including an amount of a bisphosphonate in its zwitterionic form and an amount of a phospholipid in its zwitterionic form, where the phospholipid is present in an amount sufficient to reduce a GI toxicity of the bisphosphonate and improve bisphosphonate bio-availability particularly when the composition is taken with meals, and the amount of bisphosphonate is sufficient to reduce bone resorption and/or increase bone density, particularly when the composition is taken with meals.

The present invention also provides a mixture comprising a bisphosphonate, a phospholipid and a colloidal metal, a metal complex or mixtures or combinations thereof.

The present invention provides a medicinal composition comprising a mixture including a bisphosphonate, a phospholipid and a colloidal metal, a metal complex or mixtures or combinations thereof, where the phospholipid is present in an amount sufficient to reduce a GI toxicity of the bisphosphonate and improve bisphosphonate bio-availability particularly when the composition is taken with meals, and the amount of bisphosphonate is sufficient to reduce bone resorption and/or increase bone density, particularly when the composition is taken with meals.

The present invention provides a medicinal composition comprising an inert carrier and a mixture including a bisphosphonate, a phospholipid and a colloidal metal, a metal complex or mixtures or combinations thereof, where the phospholipid is present in an amount sufficient to reduce a GI toxicity of the bisphosphonate and improve bisphosphonate bio-availability particularly when the composition is taken with meals, and the amount of bisphosphonate is sufficient to reduce bone resorption and/or increase bone density, particularly when the composition is taken with meals.

The present invention also provides an ionic associated complex comprising a bisphosphonate in its zwitterionic form, a phospholipid in its zwitterionic form and a colloidal metal, a metal complex or mixtures or combinations thereof.

The present invention provides a medicinal composition comprising a mixture including a bisphosphonate in its zwitterionic form, a phospholipid in its zwitterionic form and a colloidal metal, a metal complex or mixtures or combinations thereof, where the phospholipid is present in an amount sufficient to reduce a GI toxicity of the bisphosphonate and improve bisphosphonate bio-availability particularly when the composition is taken with meals, and the amount of bisphosphonate is sufficient to reduce bone resorption and/or increase bone density, particularly when the composition is taken with meals.

The present invention provides a medicinal composition comprising an inert carrier, a mixture including a bisphosphonate in its zwitterionic form, a phospholipid in its zwitterionic form and a colloidal metal, a metal complex or mixtures or combinations thereof, where the phospholipid is present in an amount sufficient to reduce a GI toxicity of the bisphosphonate and improve bisphosphonate bio-availability particularly when the composition is taken with meals, and the amount of bisphosphonate is sufficient to reduce bone resorption and/or increase bone density, particularly when the composition is taken with meals.

The present invention also provides a composition for treating osteoporosis comprising a pharmaceutically effective amount of a bisphosphonate to reduce bone resorption and a sufficient amount of zwitterionic phospholipid to reduce GI toxicity of the bisphosphonate.

The present invention also provides a composition for treating osteoporosis comprising a pharmaceutically effective amount of a bisphosphonate and a sufficient amount of a zwitterionic phospholipid, where the composition has reduced GI toxicity and improves survivability and bio-availability of the bisphosphonate, particularly when the composition is taken with meals.

The present invention also provides a medicinal composition comprising a carrier and a pharmaceutically effective amount a bisphosphonate and a zwitterionic phospholipid, where the zwitterionic phospholipid is present in an amount sufficient to reduce GI toxicity of the bisphosphonate and increase the bio-availability of the bisphosphonate, particularly when the composition is taken with meals.

The present invention also provides an oral medication for treating osteoporosis comprising an inert carrier and a pharmaceutically effective amount a bisphosphonate and a zwitterionic phospholipid, where the zwitterionic phospholipid reduces GI toxicity of the bisphosphonate and increases the bio-availability of the bisphosphonate, particularly when the medication is taken with meals.

The present invention also provides an oral medication for treating osteoporosis comprising a solid including an inert carrier, a zwitterionic phospholipid and a pharmaceutically effective amount of a bisphosphonate, where the zwitterionic phospholipid is in an amount sufficient to reduce GI toxicity of the bisphosphonate and increase the bio-availability of the bisphosphonate, particularly when the medication is taken with meals.

The present invention also provides an oral medication for treating osteoporosis comprising a fluid including an inert carrier, a zwitterionic phospholipid and a pharmaceutically effective amount of a bisphosphonate, where the zwitterionic phospholipid is in an amount sufficient to reduce GI toxicity of the bisphosphonate and increase the bio-availability of the bisphosphonate, particularly when the medication is taken with meals.

The present invention provides a method for treating osteoporosis comprising the step of orally administering a composition comprising a zwitterionic phospholipid and a pharmaceutically effective amount of a bisphosphonate, where the zwitterionic phospholipid is present in an amount sufficient to reduce GI toxicity of the bisphosphonate and increase the bio-availability of the bisphosphonate, particularly when administered in conjunction with food.

The present invention also provides a method for making a bisphosphonate medicinal composition with reduced GI toxicity and increase bio-availability including the step of contacting a bisphosphonate and a zwitterionic phospholipid. The method can further include the step of admixing the bisphosphonate/zwitterionic phospholipid with an inert carrier.

The present invention also provides a method for making a bisphosphonate medicinal composition with reduced GI toxicity and increase bio-availability including the step of contacting a bisphosphonate and a phospholipid under conditions sufficient to maintain the bisphosphonate and the phospholipid in their zwitterionic form during at least part of the contacting time to form a molecular association of the bisphosphonate and the phospholipid. The method can further include the step of admixing the bisphosphonate/phospholipid molecular association with an inert carrier.

The present invention also provides a method for making a bisphosphonate medicinal composition with reduced GI toxicity and increased bio-availability including the step of contacting a bisphosphonate, a phospholipid and a colloidal metal, a metal complex, metal (or polyvalent cation) containing buffer, or a mixture or combination thereof to forms a metal-mediated molecular association of the bisphosphonate and phospholipid. The method can further include the step of admixing the metal-mediated molecular association with an inert carrier.

The present invention also provides a method for making a bisphosphonate medicinal composition with reduced GI toxicity and increase bio-availability including the step of contacting a bisphosphonate, a phospholipid and a colloidal metal, metal complex, metal (or polyvalent cation) containing buffer, or a mixture or combination thereof under conditions sufficient to maintain the bisphosphonate and the phospholipid in their zwitterionic forms during at least part of the contacting to form a metal-mediated molecular association of the bisphosphonate and the phospholipid. The method can further include the step of admixing the metal-mediated molecular association with an inert carrier.

The present invention also provides a method for making a pill form of the compositions of this application by making tablets, caplets, gel caps, fluid-filled gel caps, or the like using methods well-known in the art.

DEFINITIONS

Unless otherwise stated, the following terms shall have the following meanings:

The term "fluid" means a liquid and any mixture of a liquid and a solid that has fluid attributes, e.g., flowable or having appreciable fluidity a standard temperature and pressure, including, without limitation, a dispersion of a solid(s) in a liquid, an emulsion, a slurry, a micro-emulsion, colloidal suspension, a suspension, or the like.

The term "molecular association" means a combination of two or more molecular species associated via any known stabilizing atomic or molecular level interaction or any combination thereof, where the interactions include, without limitation, bonding interactions such as covalent bonding, ionic bonding, hydrogen bonding, coordinate bonding, or any other molecular bonding interaction, electrostatic interactions, a polar or hydrophobic interactions, or any other classical or quantum mechanical stabilizing atomic or molecular interaction.

The term "animal" is defined as any species in the animal kingdom including mammals.

The term "mammal" is defined as any class of warm-blooded higher vertebrates that includes humans.

The term "phospholipid" refers any lipid or fatty acid having a covalently attached a phosphate group in the molecular structure.

The term "zwitterionic phospholipid" means a phospholipid having a proton acceptor in the molecular structure so that the phosphate group can bear a negative charge and the proton acceptor can be a positive charge due to an intramolecular acid-base reaction.

The term "bisphosphonate" refers to a class of pharmaceutical compounds active in reducing bone resorption and treating osteoporosis, which are carbon-substituted pyrosphosphate analogues.

The term "heterocyclyl" means a saturated or unsaturated 5 to 7-membered heterocyclic group with one or two rings and 1 to 3 heteroatoms, independently chosen from N, O or S.

The term "aryl" denotes a substituted or unsubstituted phenyl, furyl, thienyl or pyridyl group, or a fused ring system of any of these groups, such as naphtyl.

The term "substituted aryl" denotes an aryl group as defined above which is substituted by one or more alkyl, alkoxy, halogen, amino, thiol, nitro, hydroxy, acyl. aryl or cyano groups.

The term "colloidal metal" denotes any metal or metal-containing compound that can be formed into a colloidal suspension or dispersion.

The term "metal complex" denotes complexes of any metal classified as such in the Periodic Chart of Elements and preferably, complexes of non-alkali metals.

The term "polyvalent metal complex" denotes any complex of a metal, where the metal can have, carry or bear a positive charge greater than 1 and generally from 2 to 6.

The term "zwitterion" denotes a molecule having both a positive charged group and a negatively charged group.

The term "zwitterionic form" denotes a molecule that has a positive charged group and a negatively charged group. Generally, the reaction conditions are adjusted so that intramolecular hydrogen ion transfer can occur.

The term "pharmaceutically effective amount" denotes an amount of bisphosphonate required to cause a measurable reduction in bone resorption or a measurable increase in bone density or a measurable reduction in the incidents of bone fractures in patients taking the bisphosphonates. Additional information on the procedures used to determine a measurable affect from the administration of bisphosphonates can be found in "Effects of Risedronate Treatment on Vertebral and Nonvertebral Fractures in Women with Postmenopausal Osteoporosis: A Randomized Controlled Trial," *J. Am. Med. Assn.*, 282, 1344–1352 (1999) and "Effects of Risedronate on the Risk of Hip Fracture in Elderly Women," *New England J. Med.*, 344, 333–340 (2000), incorporated herein by reference.

DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
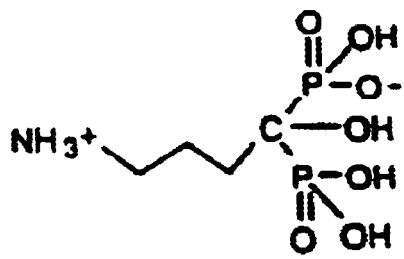
FIG. 1 illustrates similarities between bisphosphonates and zwitterionic phospholipids.
Figure 1:
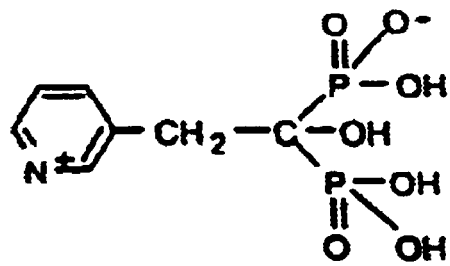
Figure 1:
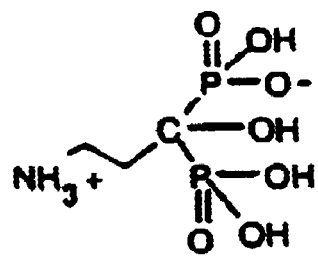
Figure 1:
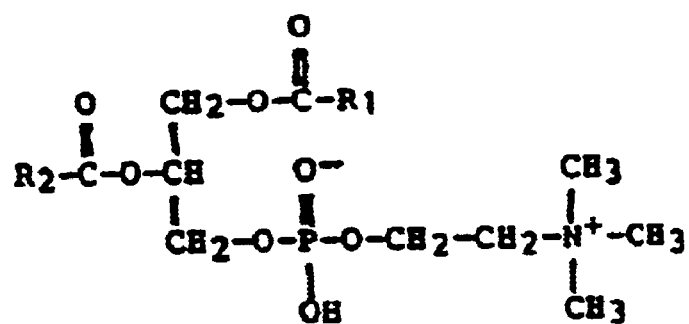

The inventor has found that unique pharmaceutical formulations including bisphosphonate compounds, which are established selective inhibitors of osteoclast-mediated bone resorption used in the treatment of osteoporosis, and a zwitterionic phospholipid such as phosphatidylcholine (PC) can be prepared, which have reduced bisphosphonate GI toxicity and/or side-effects, improved bio-availability when taken with meals, while the bisphosphonate causes increased bone density in patients suffering from osteoporosis. In both clinical and preclinical studies, it is well documented that bisphosphonates cause inflammation of, injury to and occasional ulceration of the mucosa of the upper GI tract, which limits the therapeutic usefulness of these powerful bone resorption inhibitor drugs. Moreover, studies have shown that the mucosa of the upper GI tract has hydrophobic barrier properties that are attributable to the presence of zwitterionic phospholipids, and that a number of damaging agents including, bisphosphonates may interfere with or attack this protective hydrophobic/phospholipid lining. See e.g., Lichtenberger, L M, Romero, J J, Gibson, F W, Blank M A, Dig Dis Sci 45, 1792–1801 (2000). The present invention overcomes the problems associated with standard bisphosphonate formulation by combining the bisphosphonate with a phospholipid, where the phospholipid is an amount sufficient to reduce or eliminate the bisphosphonate GI toxicity. Additionally, in clinical trials, the efficacy of bisphosphonates as effective therapeutic agents to combat osteoporosis has been well documented. See e.g., "Effects of Risedronate Treatment on Vertebral and Nonvertebral Fractures in Women with Postmenopausal Osteoporosis: A Randomized Controlled Trial," *J. Am. Med. Assn.*, 282, 1344–1352 (1999) and "Effects of Risedronate on the Risk of Hip Fracture in Elderly Women," *New England J. Med.*, 344, 333–340 (2000), incorporated herein by reference.

The present invention, therefore, relates broadly to medicinal formulations including a bisphosphonate of general formula (I):

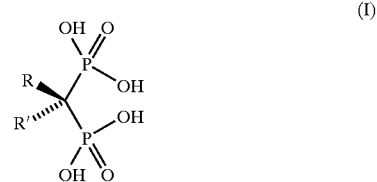

(I)

and a phospholipid of general formula (II)

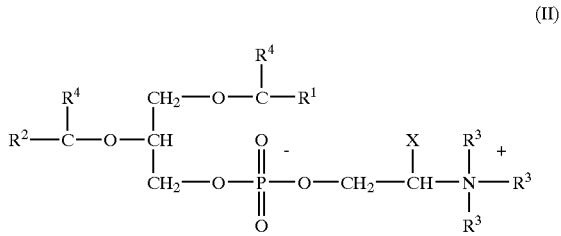

(II)

where R' is H, OH or Cl and R is: (a) an alkyl group having 1 to 6 carbon atoms, optionally substituted with amino, alkylamino, dialkylamino or heterocyclyl, where the alkyl groups in alkylamino and dialkylamino substituents have 1 to 5 carbon atoms and are the same or different in the case of the dialkylamino substituted alkyl groups; (b) a halogen; (c) an arylthio, preferably chlorosubstituted; (d) a cycloalkylamino having 5 to 7 carbon atoms; or (e) a saturated five or six membered nitrogen containing heterocyclyl having 1 or 2 heteroatoms; and $R_1$ and $R_2$ are saturated or unsaturated substitutions ranging from 8 to 32 carbon atoms; $R_3$ is H or $CH_3$, and X is H or COOH; and $R_4$ is =O or $H_2$. Mixtures and combinations of the zwitterionic phospholipids of the general formula and mixtures and combinations of bisphosphonates can be used as well.

Exemplary examples of compounds of the formula II include, without limitation, 3-amino-1-hydroxypropylidene-1,1-bisphosphonic acid (pamidronate), 4-amino-1-hydroxybutylidene-1,1-bisphosphonic acid (alendronate), N,N-dimethyl-3-amino-1-hydroxypropylidene-1,1-bisphosphonic acid (mildronate, olpadronate), I-hydroxy-3-(N-methyl-N-pentylamino) propylidene-1,(N-methyl-N-pentylamino) propylidene-1,1-bisphosphonic acid (ibandronate), I-hydroxy-2-(3-pyridyl) ethylidene-1,(3-pyridyl) ethylidene-1,1-bisphosphonic acid (risedronate), 1-hydroxyethylidene-1,1-bisphosphonic acid (etidronate), 1-hydroxy-3-(1-pyrrolidinyl) propylidene-1,1-bisphosphonic acid, 1-hydroxy-2-(1-imidazolyl) etylidene-1,1-bisphosphonic(1-imidazolyl) etylidene-1,1-bisphosphonic acid (zoledronate), 1-hydroxy-2-(imidazo [1,2-a]pyridin-3-yl) ethylidene-1,1-bisphosphonic acid (minodronate), 1-(4-chlorophenylthio) methylidene-1,1-bisphosphonic acid(tiludronate), 1-(cycloheptylamino) methylidene-1,1-bisphosphonic acid (cimadronate, incadronate), 6-amino-1-hydroxyhexylidene-1,1-bisphosphonic acid (neridronate) and pharmaceutically acceptable salts thereof or mixtures or combinations thereof.

The preferred compounds of the formula II are risedronate, alendronate, pamidronate and their pharmaceutically acceptable salts or mixtures or combinations thereof.

Exemplary examples of zwitterionic phospholipid of formula (II) include, without limitation, phosphatidyl cholines such as phosphatidyl choline (PC), dipalmitoylphosphatidylcholine (DPPC), other disaturated phosphatidyl cholines, phosphatidyl ethanolamines, phosphatidylinositol, phosphatidyl serines sphingomyelin or other ceramides, or various other zwitterionic phospholipids, phospholipid containing oils such as lecithin oils derived from soy beans or mixtures or combination thereof. The phospholipids of formula (II) can also be found in oils at various levels and such oils can also be used in the preparation of the compositions of this invention. Preferred zwitterionic phospholipid are phosphatidyl choline (PC), dipalmitoylphosphatidylcholine (DPPC), other disaturated phosphatidyl cholines, PC-containing lecithin oils or mixture or combinations thereof.

Generally, the weight ratio of bisphosphonate to zwitterionic phospholipid is between about 1:0.1 and about 1:100, with ratios between about 1:0.5 and 1:50 being preferred and ratios between about 1:1 and 1:10 being particularly preferred and ratios between about 1:1 and about 1:5 being especially preferred. The effective amount of the bisphosphonate for use in the composition of this invention ranges from about 0.1 mg per dose to about 1000 mg per dose depending on the bisphosphonate and the phospholipid used in the composition, with amounts between about 1 mg per dose to about 500 mg per does being preferred, amounts between about 2 mg per dose and 50 mg per pose being particularly preferred and amount between about 2 mg per dose and 20 mg per dose being especially preferred. A sufficient amount of phospholipid is generally an amount of phospholipid between about 0.01 mg per dose to about 5000 mg per dose, with amounts between about 0.5 mg per dose to 2500 mg per dose being preferred and amount between 2 mg per dose to about 250 mg per dose being particularly preferred and amounts between about 2 mg per dose and about 100 mg per does being especially preferred.

Generally, the compositions of this invention are formulated to be taken daily before meals, with meals and after meals. However, the formulations can also be taken more or less frequently depending on the patient and the health care provider prescribing the formulations. The preferred oral administration protocol for the compositions of this invention is a daily regiment take with or after meals.

The compositions of the present invention can be in any desirable form, including, without limitation, a solid such as a powder, granules, tablets, pills, capsules, gel coated tablets or pills, or the like, a semi-solid such as a paste or the like, a suspension, a dispersion, an emulsion, or a solution. Dispersions or suspensions means that a solid form of the compositions of the present invention are mixed with a suitable solvent in which the composition has no or relatively low solubility, i.e., a solubility less than about 10 wt. %, preferably less than about 5 wt. % and particularly less than about 1 wt. %. An emulsion means that an oil or aqueous form of the compositions of this invention are emulsified in an aqueous solution or oil, respectively, i.e. oil-in-water emulsions or water-in-oil emulsions. In addition, the emulsion can be a standard emulsion or a micro-emulsion where the emulsifying is added by passing the mixture through a nozzle or in other methods that generate micro-emulsions. A solution means that the compositions of this invention are in a suitable solvent in which the composition is soluble or highly soluble.

The present invention also broadly relates to methods for reducing bone resorption including administering a composition of this invention to a patient on a continuous or periodic basis. The composition of this invention can be administered to the patient by any known administration method including orally, with or without food, via direct injection into circulatory system (e.g., intravenous, intra-arterial, etc.), injection into soft tissue (muscle, etc.), injection into bone marrow, inhalation either into the lungs or bronchial passages or into the nasal passages, implants, or the like. Preferably, the compositions of this invention are designed for oral administration and especially for oral administration with meals.

In formulations of this invention that combine a phospholipid such as PC and a bisphosphonate such as alendronate, pamidronate or risedronate, the phospholipid acts to reduce and/or abolish the GI toxicity of the bisphosphonates. Thus, the formulations of this invention, which supplement bisphosphonates with phospholipids, show significantly less GI toxicity removing a major impediment that severely limits the utility of bisphosphonates in patients debilitated by osteoporosis. The bisphosphonate-phospholipid formulations of this invention not only have decreased GI toxicity, the formulations also increase the bio-availability of the bisphosphonates when taken with meals. Current formulations containing bisphosphonates loss all or a major part of their therapeutic effectiveness when taken with food. While not intending to be bound by any theory, it is generally thought that bisphosphonates bind with food components in such a way that they become unavailable for uptake in the small intestines. Additionally, it is thought that the phospholipid-bisphosphonate formulations of this invention improve bisphosphonate bio-availability by interfering with bisphosphonate interaction with components in food during food digestion in the stomach, permitting the bisphosphonates to pass out of the stomach in a bio-available form.

For example, the bisphosphonates (purified from commercially available material or synthesized) can be combined with different concentrations of either purified phospholipids or crude phospholipids. For example, PC is available in a purified form comprising >90% PC or in crude extracts from soy beans having PC concentrations of between about 15 wt. % to about 35 wt. % PC in the de-oiled and oiled states from American Lecithin Company. The presence of a phospholipid such as PC in the formulations of this inventions decreases GI toxicity in a manner similar to the mechanism of phospholipid reduction in adverse GI effects from NSAIDs as established in rodent animal models. See e.g.: U.S. Pat. Nos. 5,955,451; 5,763,422; 5,260,287; 5,260,284; 5,134,129; 5,043,329; 5,032,464; 4,950,658 and 4,918,063, incorporated herein by reference. Thus, the presence of a phospholipid in the compositions of this invention prevents, reduces, ameliorates or eliminates bisphosphonate-induced gastric injury, allowing increased bisphosphonate dosages to be administered and decreased dose frequencies, e.g., from one dose a day to several doses a day without increase GI toxicity.

The addition of zwitterionic phospholipids can also significantly increase the bio-availability of the bisphosphonates which in certain instances have bio-availabilities of about 5% or less necessitating a patient to take relatively large doses of the bisphosphonate on a routine basis. The zwitterionic phospholipids result in improved bio-availability of the bisphosphonates especially when taken with meals. The improved bio-availability can range between about a 2 fold increase to as much as about a 20 fold or more by judiciously choosing the bisphosphonate, the zwitterionic phospholipid and the ratio of the two ingredients.

Although many bisphosphonates are commercially available, other can be synthesized by known procedures. For example, the synthesis of bisphosphonates (diphosphonic acid analogs) are reported in U.S. Pat. Nos. 4,705,651 and 4,327,039, incorporated herein by reference, and their basic chemistry is described in standard text books. See, e.g., Van Wazer G. Compounds, Vol 1, Chemistry, pp 239–240 (1958). The bisphosphonate synthetic pathways are similar in these reference and involves treating orthophosphorous acid with a ω-amino acid (e.g., 4-aminobutyric acid, or β-alanine) with or without the use of a solvent. This reaction is followed by treatment with either $PCl_3$ or $PCl_5$ and a subsequent hydrolysis. All the steps can be performed in one-pot.

Phospholipids can either be extracted from natural sources such as lecithin oils derived from soy beans or purchased in purified form. Analogs can be prepared synthetically using known synthetic methods. For further details, see e.g.: U.S. Pat. Nos. 5,955,451; 5,763,422; 5,260,287; 5,260,284; 5,134,129; 5,043,329; 5,032,464; 4,950,658 and 4,918,063, incorporated herein by reference.

Although there has been considerable disagreement with regards to a number of issues associated with medication containing bisphosphonates such as the comparative toxicity of different bisphosphonates, relevant dosage levels, and the dependence of this injurious action on the presence of a primary amino group, the clinical, laboratory and histological evidence indicates that bisphosphonates exert gastric damage by acting as topical irritants on the gastric mucosa.

One potential mechanism by which bisphosphonates may topically injure the mucosa of the upper GI tract is by attenuating the tissues' hydrophobic barrier to luminal acid. This hydrophobic characteristic was originally described by the inventor and associates by demonstrating that a microliter droplet of water beaded up when applied to the luminal surface of canine gastric mucosa, forming a prominent contact angle at the air/liquid/solid interface. See, e.g., Hills B A, Butler B D, Lichtenberger L M, *Am J Physiol,* 244, G561–G568 (1983). Since that report, it has been demonstrated by a number of laboratories that the mucosa of specific GI tissues (e.g., stomach, distal esophagus and colon) have prominent hydrophobic properties both in laboratory animals and humans. See, e.g., Hills B A, Butler B D, Lichtenberger L M, *Am J Physiol,* 244, G561–G568 (1983), Lichtenberger L M, *Annu Rev Physiol,* 57, 565–583 (1995), Goggin P M, Marrero J M, Spychal R I, Jackson P A, Corbishley C M, Northfield T C, *Gastroenterology,* 103, 1486–1490 (1992), and Asante M, Ahmed H, Patel P, Davis T, Finlayson C, Mendall M, Northfield; Gastroenterology, 113; 449–454 (1997).

Moreover, it has been established that damaging agents such as aspirin, bile salts or the like and various conditions such as Helicobacter infection, stress or the like are associated with a clear and rapid attenuation in the hydrophobic properties of the upper GI tract. See, e.g., Hills B A, Butler B D, Lichtenberger L M, *Am J Physiol,* 244, G561–G568 (1983), Lichtenberger L M, Annu Rev Physiol, 57, 565–583 (1995), Goggin P M, Marrero J M, Spychal R I, Jackson P A, Corbishley C M, Northfield T C, *Gastroenterology,* 103, 1486–1490 (1992), Asante M, Ahmed H, Patel P, Davis T, Finlayson C, Mendall M, Northfield; *Gastroenterology,* 113; 449–454 (1997), Lichtenberger L M, Dial E J, Ottlecz A, Romero J J, Lechago J, Fox J G, *Dig Dis Sci,* 44, 108–115 (1999), Goddard P J, Hills B A, Lichtenberger L M, *Am J Physiol,* 252, G421–G430 (1987), and Lichtenberger L M, Wang Z-M, Romero J J, Ulloa C, Perez J C, Giraud M-N, Barreto J C, *Nature Med,* 1, 154–158 (1995). It should be noted that a number of substances that are used as additives to enhance drug absorption are known irritants or damaging agents of the GI mucosa, and would be contraindicated to be used together with bisphosphonates. Such substances would include: short chain fatty acids such as citric acid, decanoic acid, caprylic acid or the like; long-chain unsaturated fatty acids such as oleic acid or the like; detergents such as Brij, Tween-80, sodium deoxycholate, or like; and chelators of polyvalent metal cations such as EDTA, EGTA or the like.

The molecular basis of the hydrophobic barrier property of the upper GI tract is still unresolved, but compelling evidence indicates that zwitterionic phospholipids and specifically phosphatidylcholine (PC) may be involved. This evidence is includes: 1) the well established fact that PC and other surfactant-like polar lipids can impart hydrophobic properties to both inert and biological surfaces (Hills B A, Butler B D, Lichtenberger L M, *Am J Physiol,* 244, G561–G568 (1983) and Lichtenberger L M, Annu Rev Physiol, 57, 565–583 (1995)); 2) the findings that surface gastric mucous cells synthesize and secrete these molecules into the adherent mucus layer (Lichtenberger L M, *Annu Rev Physiol,* 57, 565–583 (1995) and Kao Y-C, Lichtenberger L M, *Gastroenterology* 101, 7–21 (1991)); 3) laboratory and clinical findings that synthetic or purified PC has the ability to protect laboratory animals and humans from certain ulcerogenic agents and/or conditions (Lichtenberger L M, *Annu Rev Physiol,* 57, 565–583 (1995), Lichtenberger L M, Graziani L A,Dial E J, Butler B D, Holls B A, Science 219; 1327–1329 (1983) and Anand B S, Romero J J, Sanduja S K, Lichtenberger L M, Am J Gastroenterol, in press (1999)).

Interestingly, the head group of PC and a number of other gastroprotective zwitterionic phospholipids have a negatively-charged phosphate group on one end and a positively-charged nitrogen group on the other, connected by a short (2-carbon length) hydrocarbon chain, somewhat similar to the charge and molecular structure of members of the bisphosphonate family of compounds. These molecular similarities between these two families of zwitterionic compounds are depicted in FIG. 1. It should be noted that the one difference between bisphosphonates and phospholipid is that bisphosphonates carry two phosphonate groups (though only one is ionized similar to the phosphate group of PC) that are generally separated from the nitrogenous group by a hydrocarbon chain containing three or more carbon atoms, while phospholipids have only a single phosphate group that are generally separated from the nitrogenous group by a hydrocarbon chain containing two or more carbon atoms.

Because the molecular properties of these two family of compounds are similar, experiments were performed to determine if bisphosphonates injure the gastric mucosa by competing with the head group of intrinsic zwitterionic phospholipids for binding sites on the surface mucus gel layer, and in doing so, reduce the tissue's protective hydrophobic barrier characteristics described previously. The experiments investigated the effects of different bisphosphonates on the surface hydrophobicity and phospholipid concentration of the antral mucosa, using the animal model of Blank et. al. (Blank M A, Ems B L, Gibson G W, Myers W R, Berman S K, Phipps R J, Smith P N, *Dig Dis Sci* 42, 281–288 (1997)), and compared the effects of these surface changes to the gastric toxicity of these drugs.

Figure 2:
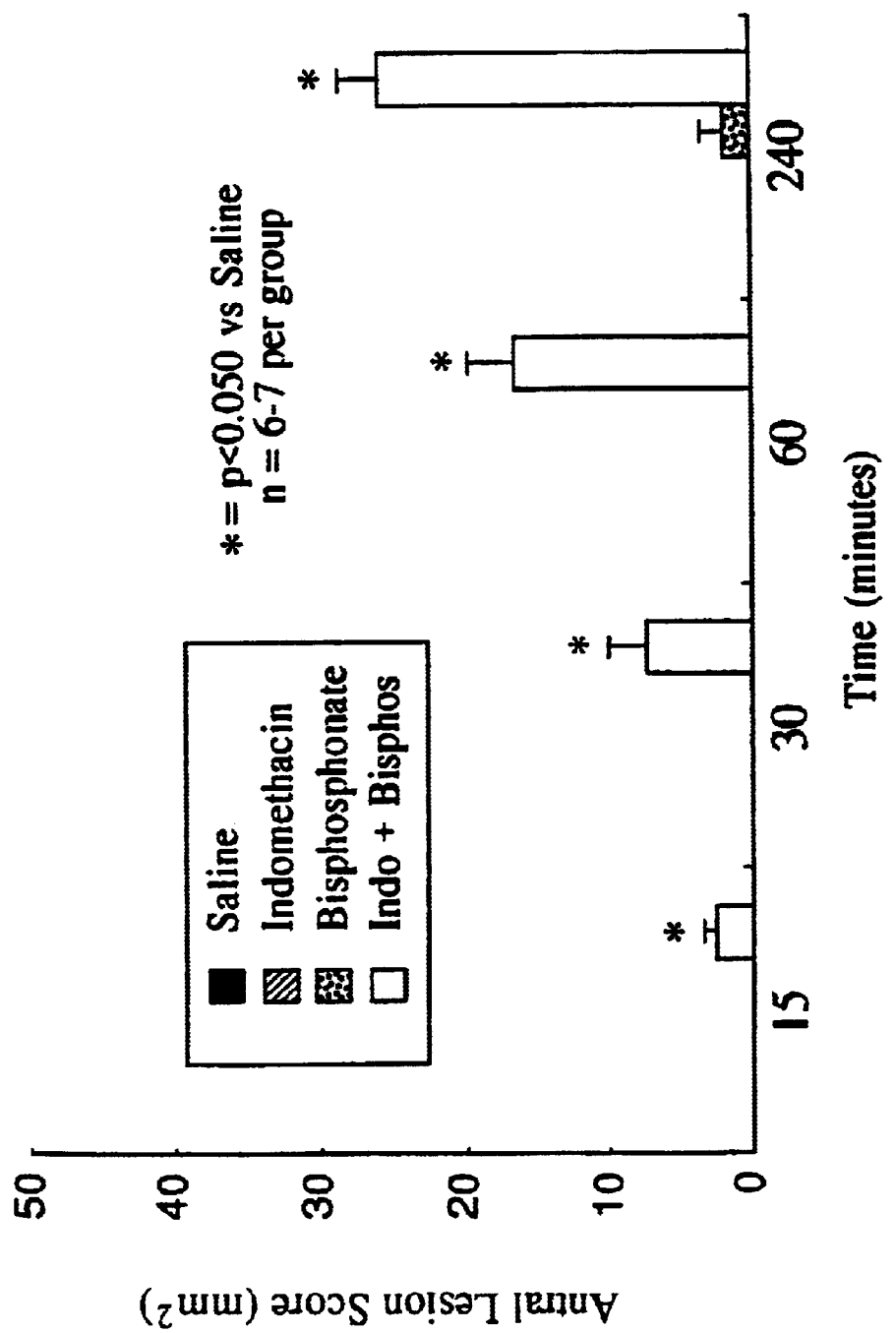
FIG. 2 demonstrates that pamidronate induced lesions in both the antrum and body of the rat stomach over a 4 hr period, when administered in combination with indomethacin.

In these rodent studies, the inventor initially focused on pamidronate, a bisphosphonate which no longer is dispensed for oral administration due to GI side-effects, and demonstrated that pamidronate induced lesions in both the antrum and body of the rat stomach over a 4 hr period, when administered in combination with indomethacin. Looking at FIG. 2, an antrum lesion score is plotted against time.

Figure 3A:
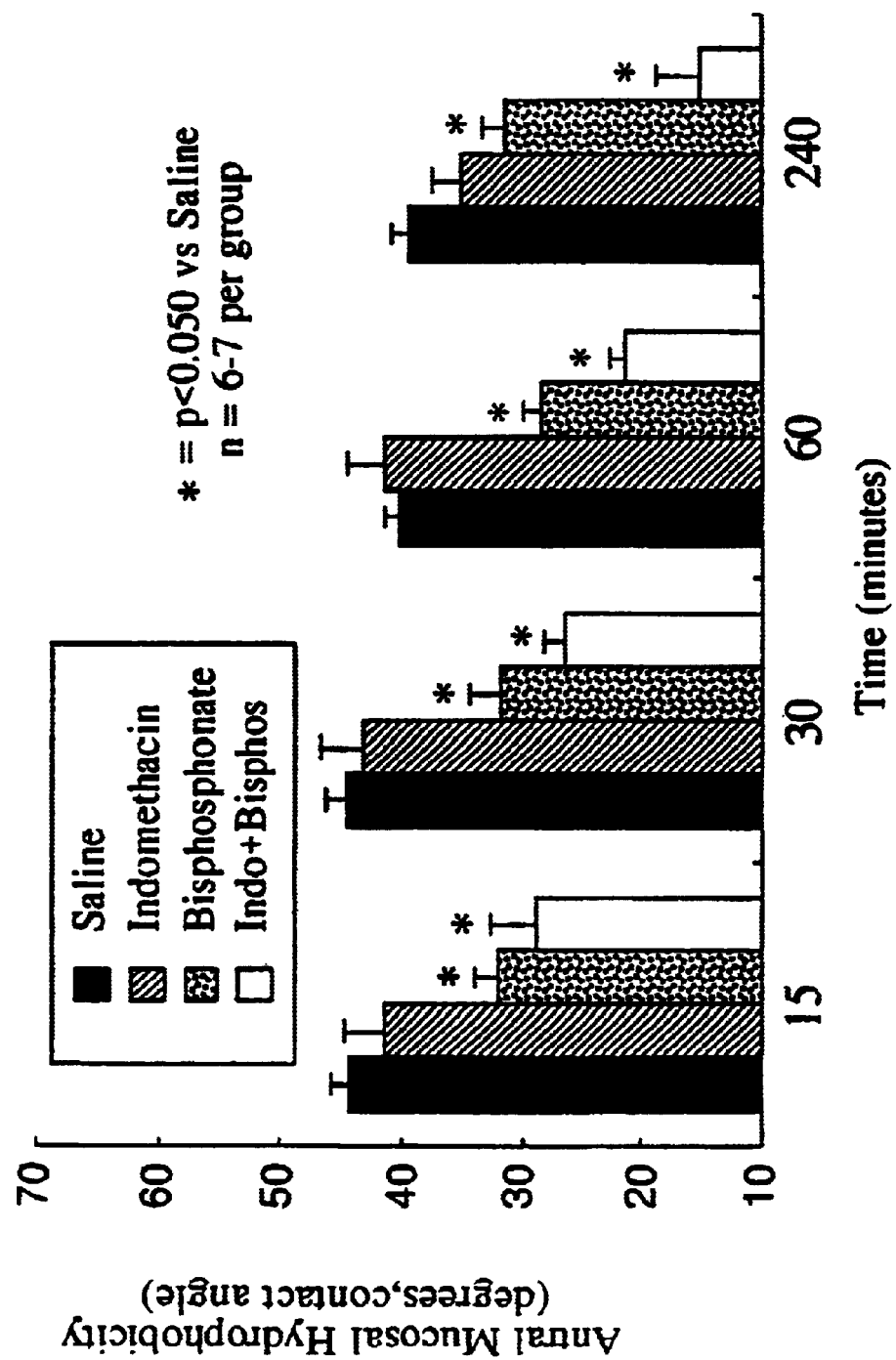
FIGS. 3A and 3B depict reductions in the stomachs' hydrophobic/phospholipidic barrier occurred rapidly (30–60 min) and were more prominent than that recorded in response to either the bisphosphonate or the NSAID alone.
Figure 3B:
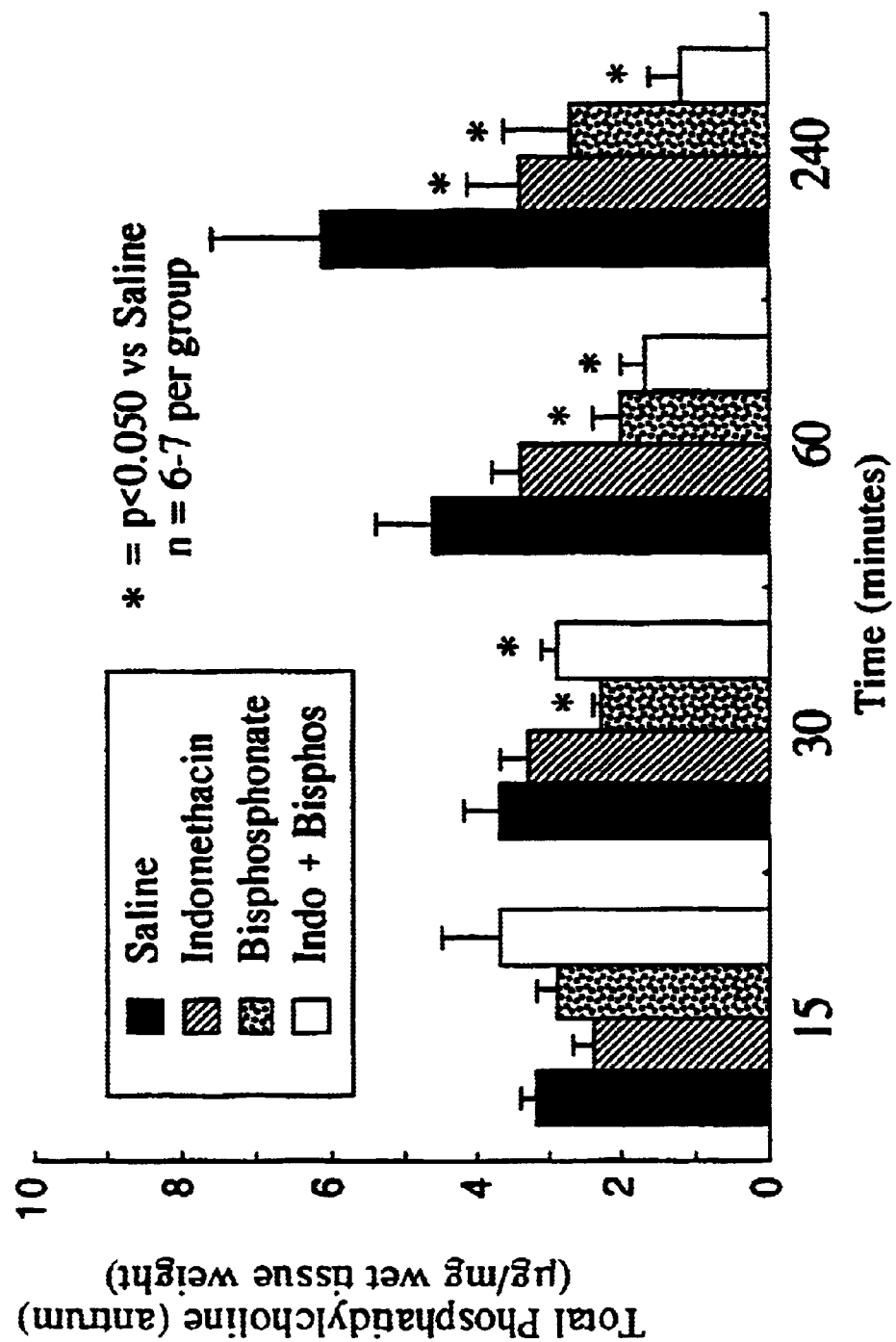

Moreover, it was also demonstrated that the combination of pamidronate and indomethacin was very effective in attenuating both the hydrophobic characteristics and intrinsic phospholipid (PC) concentration of the gastric mucosa. It was notable that these reductions in the stomachs' hydrophobic/phospholipidic barrier occurred rapidly (30–60 min) and were more prominent than that recorded in response to either the bisphosphonate or the NSAID alone as shown in FIGS. 3A & B, similar to the development of gastric lesions.

Figure 4:
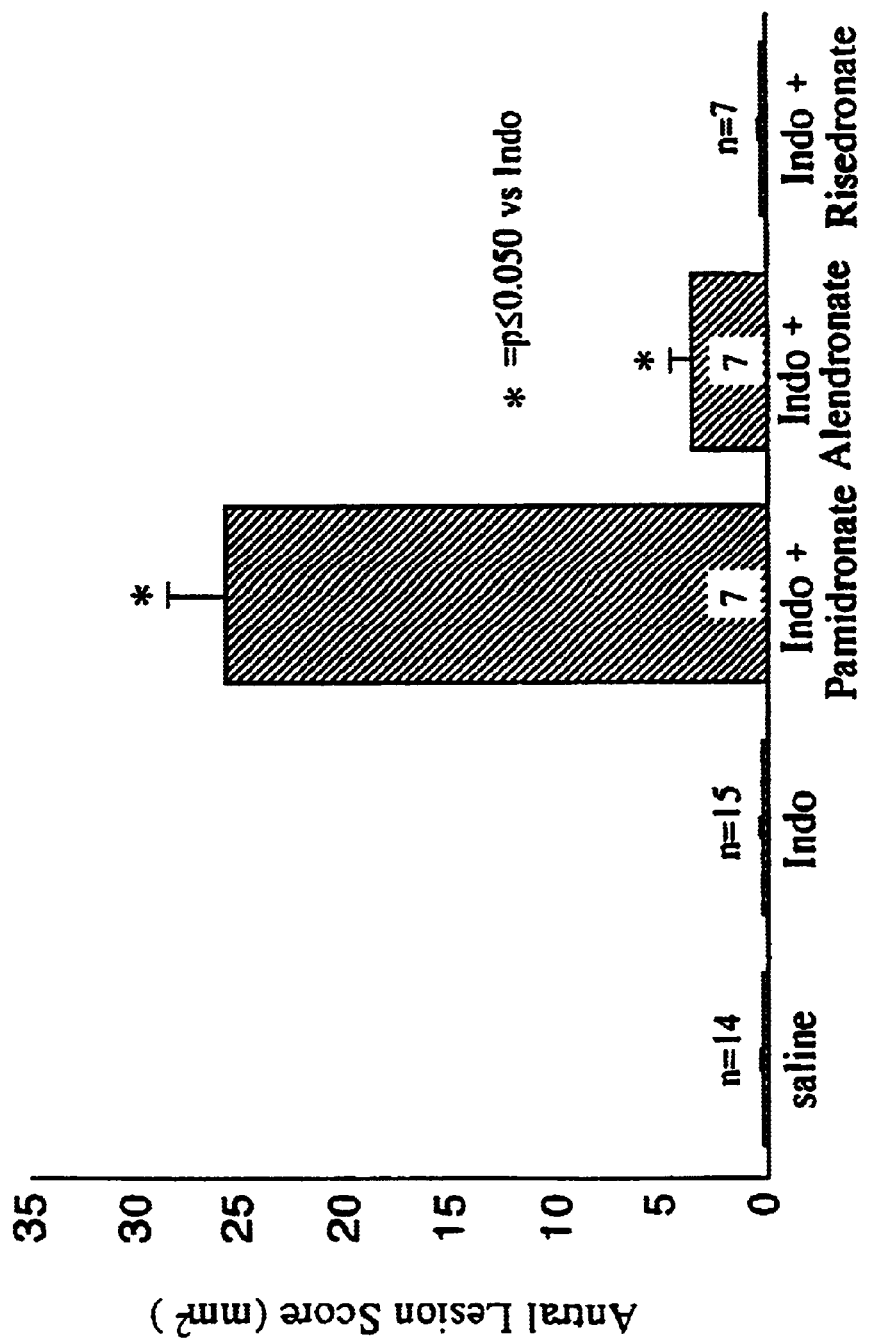
FIG. 4 depicts the gastrotoxicity of three different bisphosphonates, pamidronate>>alendronate>risedronate.
Figure 5:
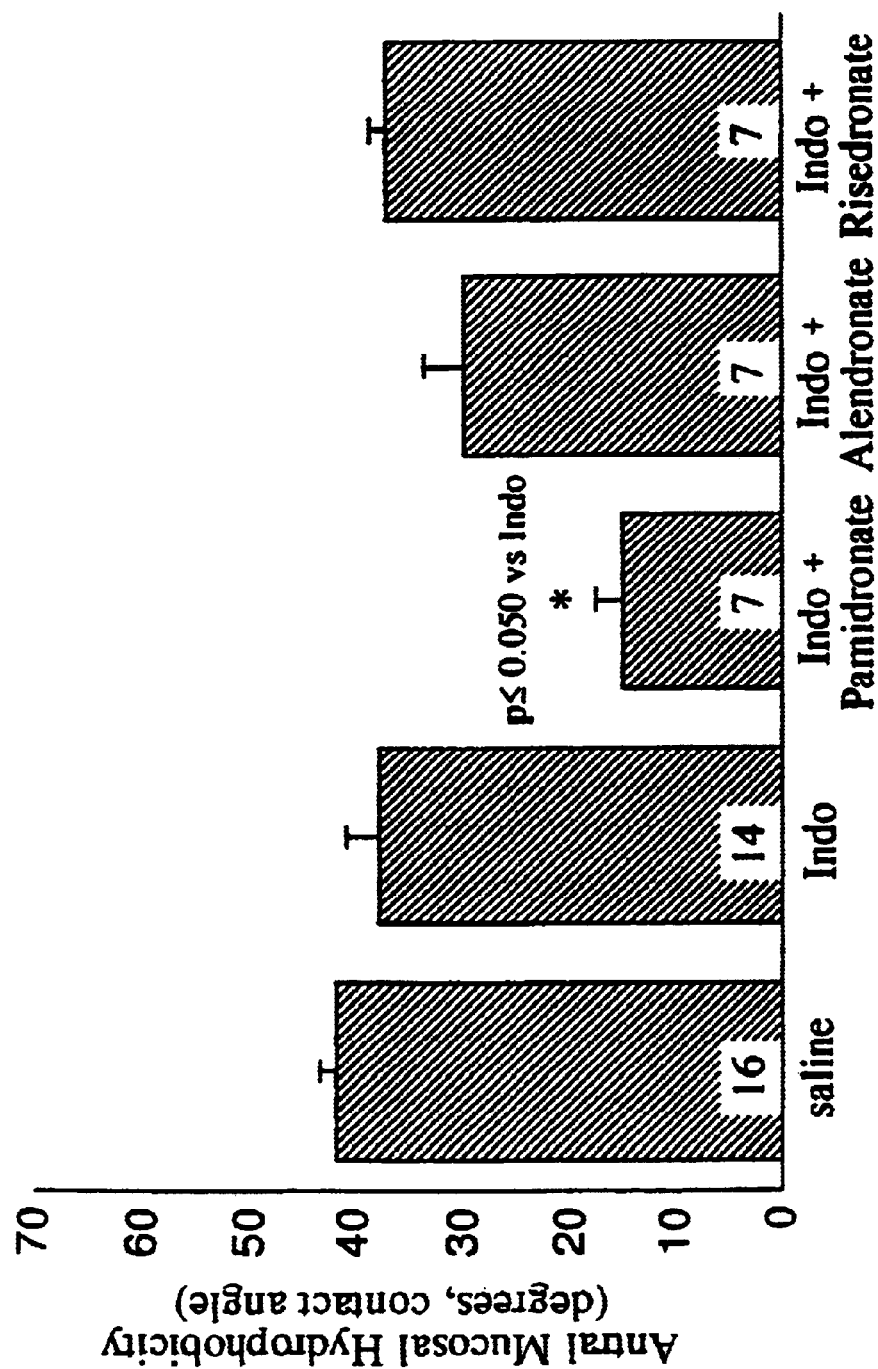
FIG. 5 depicts the attenuated stomach's hydrophobic phospholipid barrier property caused by the bisphosphonates of FIG. 4.

When pamidronate, alendronate and risedronate were compared, it was found that the order of their gastrotoxicity is pamidronate>>alendronate>risedronate as shown in FIG. 4, which is maintained in the bisphosphonates' ability to attenuate the stomach's hydrophobic phospholipid barrier property as shown in FIG. 5. Histological studies indicated that even the least gastrotoxic bisphosphonate, risedronate, induced some surface injury to the gastic mucosa. Moreover, regression analysis revealed that the bisphosphonates' ability to induce gastric lesions was significantly associated with their ability reduce the stomachs' protective hydrophobic characteristics (r=0.6, p<0.001).

Figure 6:
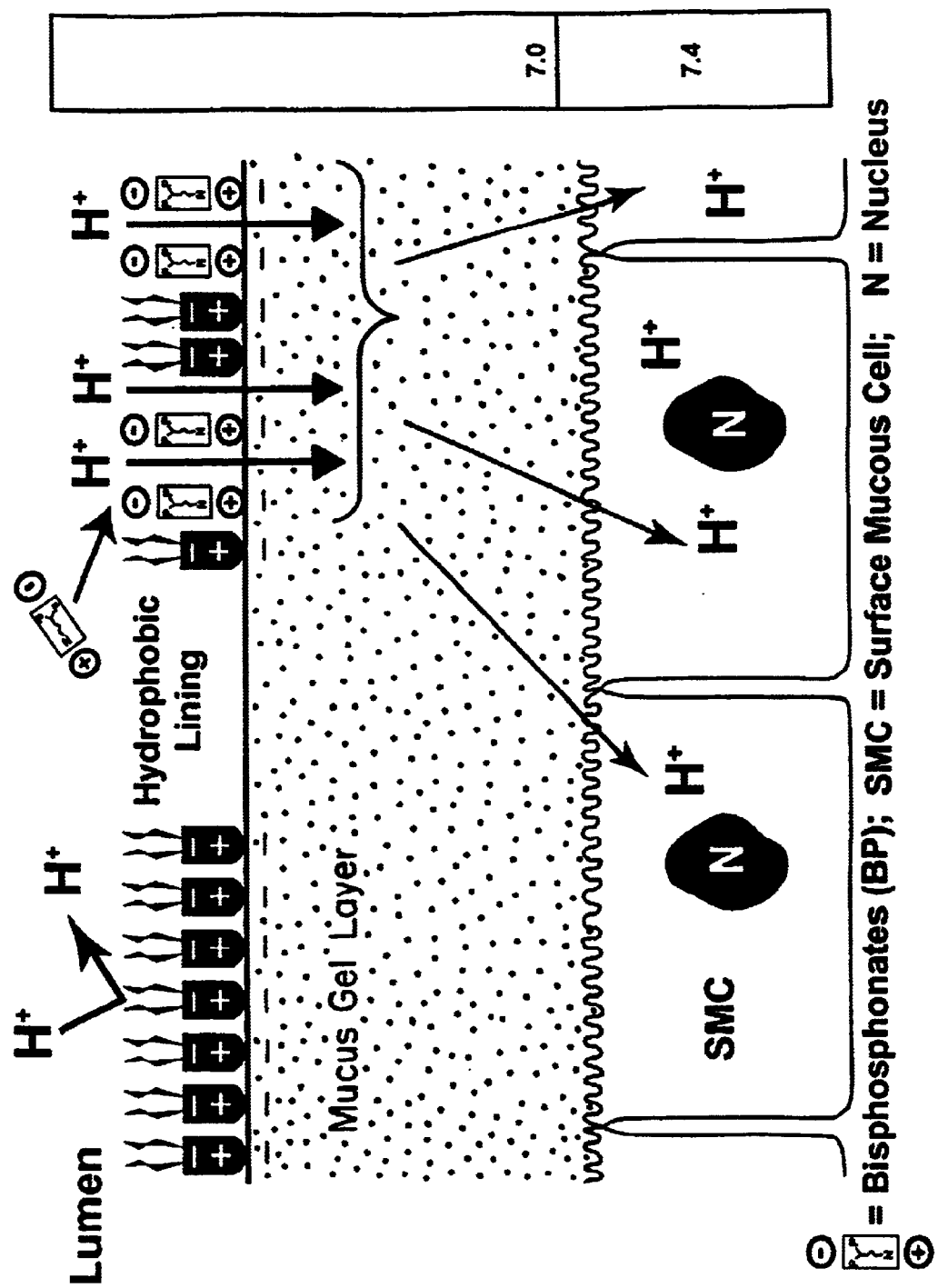
FIG. 6 depicts data that supports a model that bisphosphonates induce surface injury by competitively displacing PC and related phospholipids from the surface of the mucus gel layer, due to the common zwitterionic nature of both classes of compounds.

This data supports a model of bisphosphonate GI toxicity depicted in FIG. 6, where the bisphosphonates induce surface injury by competitively displacing intrinsic surface phospholipid (such as PC) and related phospholipids from the surface of the mucus gel layer, due to the similar zwitterionic nature of bisphosphonates and phospholipids such as PC. However, unlike phospholipid surface binding, the bisphosphonates would result in the formation or insertion of hydrophilic water channels in the hydrophobic lining of the upper GI tract, allowing HCl and other noxious, water-soluble compounds to back-diffuse from the lumen into the tissue to induce mucosal injury and inflammation.

Figure 7:
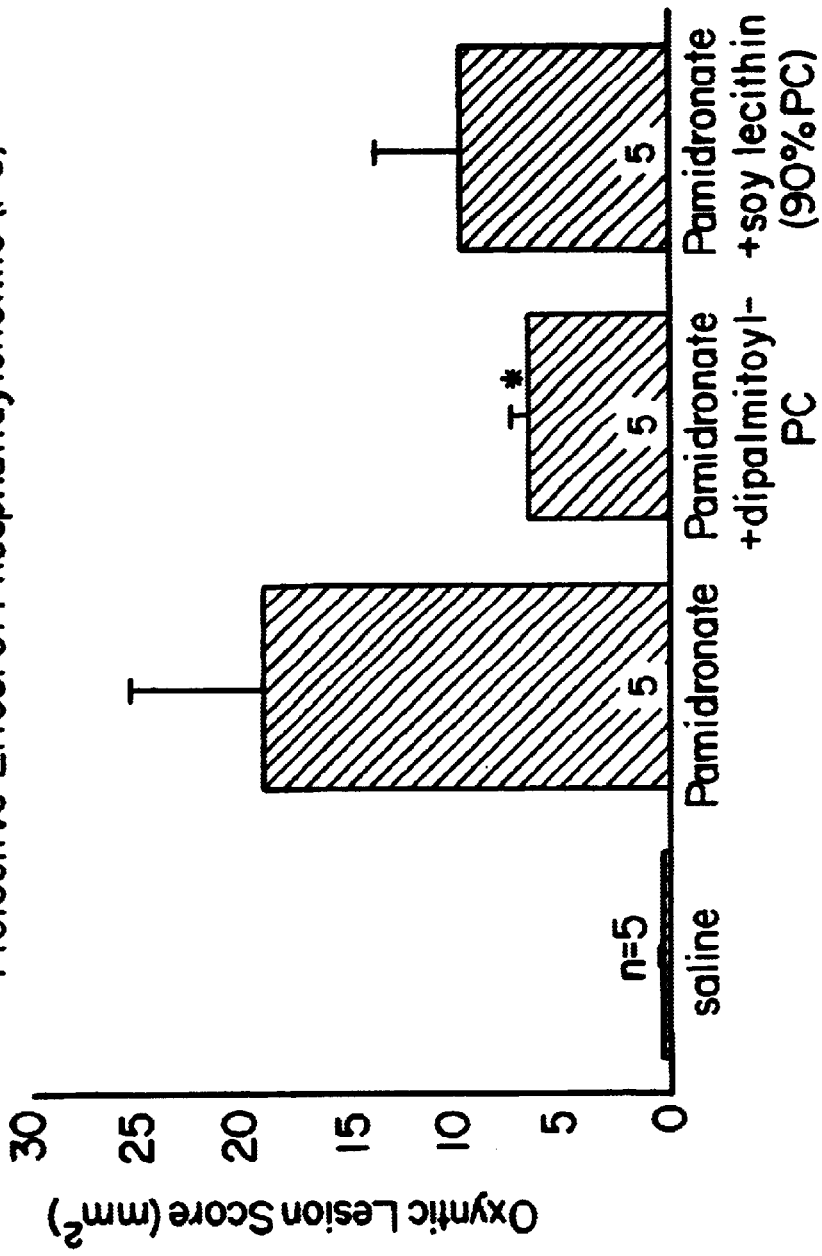
FIG. 7 depicts that the gastric lesion score induced by combinations of indomethacin and pamidronate are significantly reduced by PC supplementation.

Although not intending to be bound by any theory or model, the above model is consistent with the bisphosphonates GI toxicity and is consistent with the ability for phospholipid/bisphosphonate medications of this invention to reduce and/or prevent surface injury, and the resultant mucosal inflammation. The model and the ability for phospholipids to inhibit bisphosphonate GI toxicity was investigated in pilot preclinical studies using the rodent model of Blank et. al. (Blank M A, Ems B L, Gibson G W, Myers W R, Berman S K, Phipps R J, Smith P N, *Dig Dis Sci.* 42, 281–288 (1997)), where the bisphosphonate test drug was administered simultaneously with indomethacin. The examples compared the gastric toxicity of pamidronate alone to formulations where pamidronate was combined with either synthetic dipalmitoyl-PC (DPPC) or 90% PC (purified from soy lecithin) at a bisphosphonate to PC weight ratio of 1.0:0.3. As shown in FIG. 7, PC supplementation significantly reduced the gastric lesion score induced by pamidronate, even at the rather low ratio use. Purified soy lecithin (containing 90–93% PC) also showed considerable gastroprotective efficacy against pamidronate/indomethacin—induced gastric injury. A 1:1 weight ratio of pamidronate to PC also resulted in a significant reduction in gastric lesion score and a marked reduction in gastric bleeding in comparison to that induced by the pamidronate as tabulated Table 1.

TABLE 1

Comparison of gastric lesion score and bleeding of rats administered PC-pamidronate vs pamidronate alone.

| Groups | Gastric Lesion Score (lesioned area, mm$^2$) | Gastric Bleeding (mg Hb in perfusate) |
|---|---|---|
| Saline | 0 ± 0 | 0.2 ± 0.1 |
| Indomethacin (Indo, 40 mg/kg) | 0 ± 0 | 0.3 ± 0.1 |
| Pamidronate (300 mg/kg) + Indo | 62 ± 11* | 6.4 ± 1.9* |
| PC-Pamidronate + Indo | 31 ± 5*♦ | 1.2 ± 0.3*♦ |

*= p < 0.05 vs Indo; ♦= p < 0.05 vs pamidronate + Indo, n = 4–5 rats/group

Subsequent experiments demonstrated that gastric lesions in response to combinations of alendronate and indomethacin, were completely prevented if the bisphosphonate was intragastrically administered in formulations containing increasing amounts of 90–93% PC (purified from soy lecithin). Looking at FIG. 8, alendronate-induced lesion scores were significantly reduced with alendronate to PC weight ratios of 1:1 and 1:4, with the 1:4 ratio showing a slight more reduction than the 1:1 ratio.

METHODS FOR MAKING AND EXAMPLES

Methods for Making Bisphosphonate/Phospholipid Compositions

One preferred class of compositions of this invention are compositions that include a bisphosphonate and a phospholipid generally prepared by contacting a bisphosphonate and a phospholipid under conditions to promote molecular association of the bisphosphonate and phospholipid in their zwitterionic forms. Such conditions typically will include use of a solvent and/or buffer, use of mixing procedures that promote molecular interactions and associations, and controlled temperature, pressure and time to permit a desired degree of intermolecular interaction and association. Because these two classes of chemicals can exist as zwitterions in polar solvents, intermolecular interactions and associations between these two classes of compounds can be facilitated either by using a solvent or by using a buffer of low ionic strength, so called hypotonic buffers. In some cases, the bisphosphonate will be added to the PC or deoiled lecithin in the organic solvent prior to its removal by evaporation.

Generally, the hypotonic buffers include water with buffering compounds added to from a buffer having a molarity of between about 1 millimolar to about 100 millimolar. These low ionic strength buffers promote intermolecular interactions and/or associations between the zwitterionic forms of the bisphosphonate and phospholipid by reducing interactions between the bisphosphonate and the buffer and the phospholipid and the buffer.

The contacting is also performed in the presence of mixing, and preferably aggressive or vigorous mixing. Such mixing procedures include sonication or other molecular level mixing procedures, vortex mixing or other high shear mixing procedures, or the like. The time and temperature of mixing should be designed to maximize intermolecular interactions between the zwitterionic forms of the bisphosphonate and the phospholipid without causing thermal or shear damage to the molecules themselves. Generally, the mixing time will range from about 5 minutes to several hours, with times ranging between 10 minutes and 1 hour being preferred. Generally, the mixing temperature will range from ambient to a temperature at least 10% below the lowest breakdown temperature for the bisphosphonate or phospholipid being mixed or at least 10% below the boiling point of the lowest boiling solvent or 10% below a temperature at which the buffer begins to decompose or loss its buffering capacity. Preferably, the temperature will be between ambient temperature to about 70° C.

The pH of the buffer can also play a role in the promotion of intermolecular interactions and/or associates between the bisphosphonate and phospholipid. Generally, the pH should be controlled to ensure that the bisphosphonate and phospholipid exist in their zwitterionic forms. Generally, the pH should range between about 3 and about 10, and preferably between about 5 and 8, with a pH near 7 being particularly preferred.

In preparing the formulations of this invention, the bisphosphonates can be mixed with purified naturally derived or synthetic phospholipid or can be mixed with various grades of lecithin (extracted from soy lecithin available from American Lecithin Co) or other natural oils high in phospholipids. Especially useful lecithins have phospholipid concentrations ranging from about 15 to about 93% PC by weight. Moreover, the formulations can use either de-oiled and oiled-based lecithin preparations.

Regardless of the form of the phospholipid, generally the ratio of bisphosphonate to phospholipid ranges from about 1.0:0.1 to about 1:100, preferably, from about 1.0:0.5 to about 1:25, and particularly from about 1.0:1.0 to about 1.0:10.0.

In formulations using deoiled lecithins, the deoiled lecithins are initially dissolved in an organic solvent such as ethanol, lyophilized to remove the organic solvent and then resuspended in a bisphosphonate containing solution, followed by mixing such as vortexing and/or sonication mixing. In formulations using lecithins, the oiled-based lecithin is simply combined with a bisphosphonate compounds and mixed by vortexing and/or sonication, if needed.

Another preferred method for making the compositions of this invention is to dissolve the bisphosphonates in hypotonic aqueous solution or buffer having a molarity between about 1 and about 100 millimolar (mM). Suitable solutions and/or buffers include, without limitation, NaCl solutions, Tris buffers, bicarbonate buffers, HEPES buffers, MOPS buffers or the like.

Sonication or mixing temperatures are preferably preformed at a temperature above the transition temperature, $T_m$, of the phospholipid, i.e., the temperature at which the phospholipid undergoes a phase transitions from a liquid crystalline state to a gel state as is well-known in the art). In the case of PC, the mixing can be performed at room temperature, while for DPPC, the mixing is performed above 42° C.

Another preferred process for making the compositions of this invention includes to dissolving the phospholipid and the bisphosphonate in a polar solvent. Suitable solvent include, without limitation, chlorocarbons such as chloroform, or the like, lower alcohols such as methanol, ethanol, isopropanol or the like, or any other solvent in which the phospholipid and the bisphosphonate have some solubility, with the added condition that the solvent be readily removable by either evaporation or the like.

When a metal complex is used, the complex can be added directly into the phospholipid and the bisphosphonate solution. Alternatively and preferably, the complex and the bisphosphonate can be prepared in a hypotonic buffer that is added a preformed phospholipid film as described herein.

EXAMPLES

The following examples are included for the sake of completeness of disclosure and to illustrate the preparation of compositions of present invention containing a bisphosphonate and a phospholipid, but in no way are these examples included for the sake of limiting the scope or teaching of this disclosure.

Example 1

This example illustrates the preparation of a composition of pamidronate and dipalmitoyl-PC.

60 mg of Phospholipon 90G (90–93% pure PC) was dissolved in chloroform in a tube. Although chloroform was used, ethanol works as well. The organic solvent was removed under nitrogen and resulting PC material was left under vacuum overnight to form a PC film in the tube. Pamidronate was dissolved in saline and the resulting solution was adjusted to pH 7.0. The solution was then added to the dried PC film in the tube. The mixture was sonicated in a both type sonicator at room temperature for 5 min., prior to administration to fasted rats. The results of this example are reported in Table 1 and were described previously. A thin film of the phospholipid is thought to increase interactions between the phospholipid and bisphosphonates.

Example 2

This example illustrates the preparation of a composition of pamidronate and dipalmitoyl-PC.

20 mg of dipalmitoyl PC (DPPC) and Phospholipon 90G were dissolved in chloroform in separate tubes, and dried as described in Example 1. A solution of 60 mg/mL of pamidronate in saline adjusted to pH 7 was prepared and added to each of the tubes, one containing the DPPC film and the other containing the PC film. The PC-pamidronate mixture was then sonicated for 5 min. at room temperature, while the DPPC-pamidronate mixture was sonicated for 5 min. at a temperature above 42° C., about 45°. The results of the example are shown in FIG. 7 and described previously.

Example 3

This example illustrates the preparation of a composition of pamidronate and dipalmitoyl-PC.

Figure 8:
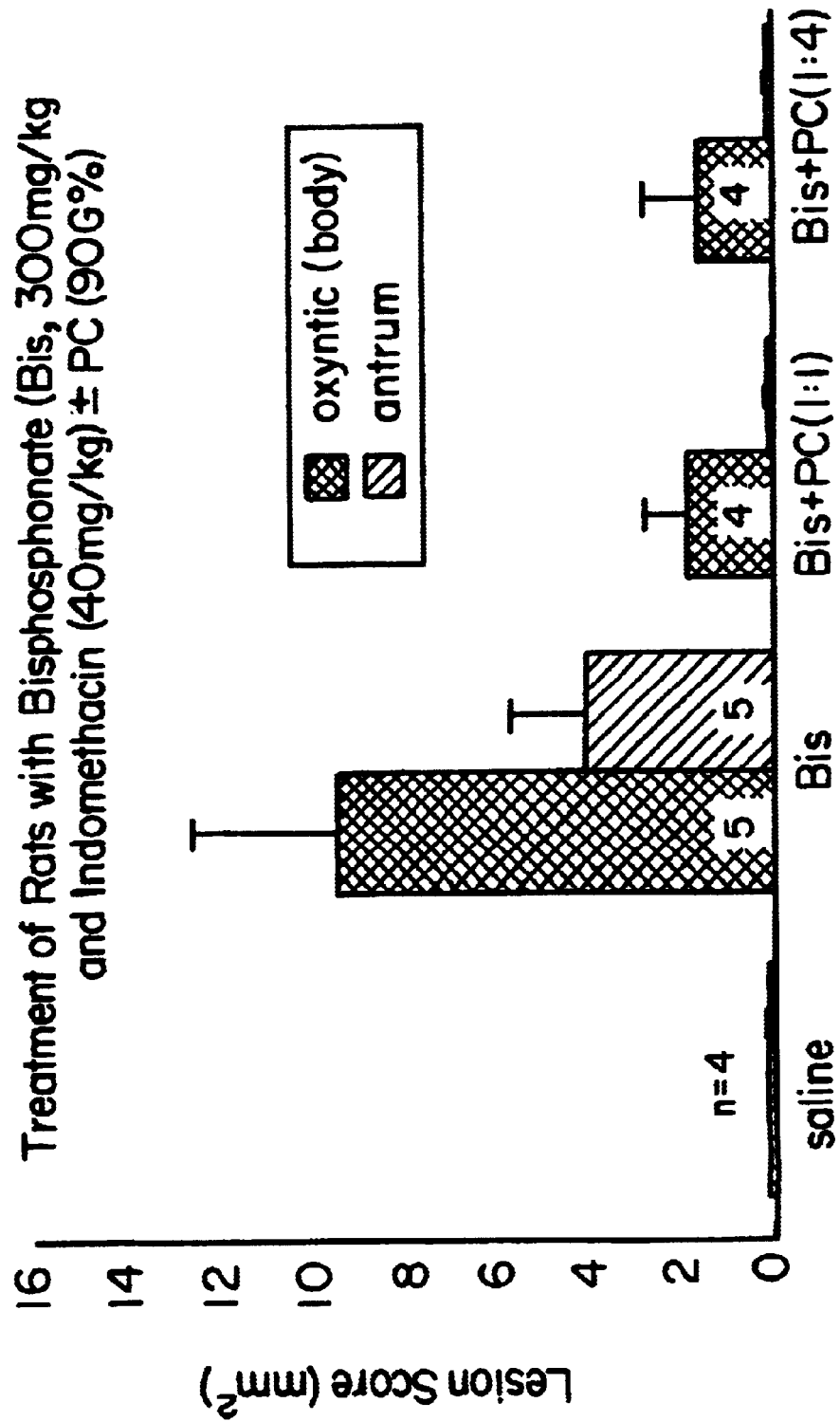
FIG. 8 depicts the prevention of gastric lesions in response to combinations of alendronate and indomethacin, if the bisphosphonate was intragastrically administered in formulations containing increasing amounts of 90–93% PC (purified from soy lecithin) employing alendronate to PC weight ratios of 1:1 and 1:4.

60 mg and 240 mg of Phospholipon 90G were dissolved in chloroform and dried as described in Example 1 in separate tubes. A solution of 60 mg/mL of alendronate in saline adjusted to pH 7 was prepared and added to the tubes containing the dried PC film. The mixture as was sonicated for 5 min. at room temperature The results of the example are shown in FIG. 8 and described previously.

Methods for Making Metal-Mediated Bisphosphonate/Phospholipid Compositions

Another preferred class of compositions of this invention are compositions that include a bisphosphonate, a phospholipid and a metal complex or a colloidal metal, which are generally prepared by contacting a bisphosphonate, a phospholipid and a metal complex or colloidal metal under conditions to promote molecular association of the bisphosphonate and the phospholipid in their zwitterionic forms and the two compounds of the metal complex or colloidal metal. Such conditions typically will include use of a solvent and/or buffer, use of mixing procedures that promote molecular interactions and associations, and controlled temperature, pressure and time to permit a desired degree of intermolecular interaction and/or association. Because bisphosphonates and phospholipids can exist as zwitterions in polar solvents, intermolecular interactions and/or associations between bisphosphonates and phospholipid can be facilitated either by using a solvent or by using a buffer of low ionic strength, so call hypotonic buffers. In addition, under these conditions, the metal complex and/or colloidal metal can help form compositions of bisphosphonates and phospholipids that can make the bisphosphonate available for absorption into the blood stream via the intestinal wall even after ingestion with food.

Generally, these buffers will include water with buffering compounds added to from a buffer having a molarity of between about 1 to about 100 millimolar. These low ionic strength buffers will promote intermolecular interaction and/ or associations between the zwitterionic forms of the bisphosphonate and phospholipid by reducing interactions between the bisphosphonate and the buffer and the phospholipid and the buffer. For compositions including metal complexes, the buffer can be formed using the same metal.

In some cases, polyvalent cations or colloidal metals will be added to either the organic solvent (prior to its removal by evaporation) or more likely to the aqueous solution containing the bisphosphonate that is added to the PC-containing lipid film to promote the bonding of the two classes of zwitterionic compounds. For polyvalent metals such aluminum, gold, bismuth or other polyvalent metals, the pH is preferably adjusted to ensure that the metal is soluble and active and the bisphosphonate and phospholipid are in their zwitterionic forms. The active pH range for these polyvalent metal complexes is generally between about 2.5 and 5, which is a range in which the bisphosphonate and phospholipid are in their zwitterionic forms.

The contacting is also performed in the presence of mixing, and preferably aggressive or vigorous mixing. Such mixing procedures include sonication, vortex mixing or other high shear mixing procedures. The time and temperature of the mixing should be designed to maximize intermolecular interactions between the zwitterionic forms of the bisphosphonate and the phospholipid without causing thermal or shear damage to the molecules themselves. Generally, the mixing time will range from about 5 minutes to several hours, with times ranging between 10 minutes and 1 hour being preferred. Generally, the mixing temperature will range from ambient temperature to a temperature at least 10% below the lowest breakdown temperature for the bisphosphonate or phospholipid being mixed. Preferably, the temperature will be between ambient temperature to about 70° C.

The pH of the buffer can also play a role in the promotion of intermolecular interactions and/or associates between the bisphosphonate and phospholipid. Generally, the pH should be controlled to ensure that the bisphosphonate and phospholipid exist in their zwitterionic form. Preferably, the pH should range between about 2.5 and about 10, and particularly between about 3 and 8.

In preparing the formulations of this invention, the bisphosphonates can be mixed with purified naturally derived or synthetic phospholipid or can be mixed with various grades of lecithin (extracted from soy lecithin available from American Lecithin Co) ranging in purity from about 15 to about 93% PC by weight. Moreover, the formulations can be either de-oiled and oiled lecithin preparations. The general weight ratios of bisphosphonate to phospholipids range from about 1.0:0.1 to about 1:100, preferably, from about 1.0:0.5 to about 1:50, and particularly from about 1.0:1.0 to about 1.0:10.0 and especially from about 1:1 to about 1:5. Generally, the metal-containing component (complex or colloidal) is present in weight ratios of the sum of the amount of bisphosphonate and phospholipid to metal-containing component of about 1.0:0.01 to about 1.0:5.0, with ratios between about 1.0:0.1 and about 1.0:2.0 being preferred and ratios between about 1.0:0.5 and about 1.0:1.0 being particularly preferred.

In formulations using de-oiled lecithins, the de-oiled lecithins are initially dissolved in an organic solvent such as ethanol, lyophilized to remove the organic solvent and then re-suspended in the bisphosphonate containing solution, followed by mixing such as vortexing and/or sonication mixing. In formulations using oiled lecithins, the oiled lecithins are simply combined with the bisphosphonate compounds and mixed by vortexing and/or sonication, if needed.

Additionally, the metal-mediated composition of this invention can be prepared using if metal complexes commonly used in antacids including, without limitation, aluminum hydroxide, magnesium hydroxide, magnesium carbonate, magnesium silicate ($Mg_2Si_3O_8$), magnesium phosphate, calcium carbonate, simethicone or other silicon-containing agents, bismuth subsalicylate, bismuth subcitrate, similar bismuth antacids, or mixtures or combinations thereof, with or without the addition of a sodium source.

Suitable metal colloids include, without limitation, colloidal gold, colloidal silver, colloidal bismuth, and mixture or combinations thereof.

Suitable metal complexes include, without limitation, non-toxic metal complexes such as complexes of aluminum, magnesium, calcium, bismuth, barium, or the like where the complexes can be a hydroxide, a carbonate, a citrate, a tartarate, salicylate, or other similar bio-compatible counterions.

Methods for Making Supported Bisphosphonate/ Phospholipid Compositions

Another preferred class of compositions of this invention are compositions that include a bisphosphonate/ phospholipid mixture deposited on a non-toxic, biocompatible oxide support, which are generally prepared by contacting a bisphosphonate and a phospholipid under conditions to promote molecular association of the bisphosphonate and phospholipid in their zwitterionic forms and then adding either a particulate form of the oxide or a sol form of the oxide. The conditions to form the bisphosphonate-phospholipid mixtures are as set forth previously, while the metal oxide or sol can either be added concurrent with the bisphosphonate and phospholipid or preferably after formation of the bisphosphonate-phospholipid mixture. Again, the process typically includes use of a solvent and/or buffer, use of mixing procedures that promote molecular interactions and associations, and controlled temperature, pressure and time to permit a desired degree of intermolecular interaction and association. Because these two classes of chemicals generally exist as zwitterions in polar solvents, intermolecular interactions and associations between the to classes of compounds can be facilitated either by using a solvent or by using a buffer of low ionic strength, so call hypotonic buffers.

Generally, these buffers will include water with buffering compounds added to from a buffer having a molarity of between about 1 to about 100 millimolar. These low ionic strength buffers will promote intermolecular interaction and/ or associations between the zwitterionic forms of the bisphosphonate and phospholipid by reducing interactions between the bisphosphonate and the buffer and the phospholipid and the buffer.

The contacting is also performed in the presence of mixing, and preferably aggressive mixing. Such mixing procedures include sonication, vortex mixing or other high shear mixing procedures. The time and temperature of the mixing should be designed to maximize intermolecular interactions between the zwitterionic forms of the bisphosphonate and the phospholipid without causing thermal or shear damage to the molecules themselves. Generally, the mixing time will range from about 5 minutes to several hours, with times ranging between 10 minutes and 1 hour being preferred. Generally, the mixing temperature will range from ambient temperature to a temperature at least 10% below the lowest breakdown temperature for the bisphosphonate or phospholipid being mixed. Preferably, the temperature will be between ambient temperature to about 70°.

The pH of the buffer can also play a role in the promotion of intermolecular interactions and/or associates between the bisphosphonate and phospholipid. Generally, the pH should be controlled to ensure that the bisphosphonate and phospholipid exist in their zwitterionic form. Preferably, the pH should range between about 2.5 and about 10, and particularly between about 5 and 8. Again, for polyvalent metals such aluminum, gold, bismuth or other polyvalent metals, the pH is preferably adjusted to ensure that the metal is soluble and active and the bisphosphonate and phospholipid are in their zwitterionic forms. The active pH range for these polyvalent metal complexes is generally between about 2.5 and 5, which is a range in which the bisphosphonate and phospholipid are in their zwitterionic forms.

In preparing the formulations of this invention, the bisphosphonates can be mixed with purified naturally derived or synthetic phospholipid or can be mixed with various grades of lecithin (extracted from soy lecithin available from American Lecithin Co) ranging in purity from about 15 to about 93% PC by weight. Moreover, the formulations can be either de-oiled and oiled lecithin preparations. The general weight ratios of bisphosphonate to phospholipids range from about 1.0:0.1 to about 1:100, preferably, from about 1.0:0.5 to about 1:50, and particularly from about 1.0:1.0 to about 1.0:1 0.0 and especially from about 1.0:1.0 to about 1.0:5.0. Generally, the support material (oxide or sol) is present in weight ratios of the sum of the amount of bisphosphonate and phospholipid to support material of about 1.0:0.01 to about 1.0:5.0, with ratios between about 1.0:0.1 and about 1.0:2.0 being preferred and ratios between about 1.0:0.5 and about 1.0:1.0 being particularly preferred.

In formulations using deoiled lecithins, the deoiled lecithins are initially dissolved in an organic solvent such as ethanol, lyophilized to remove the organic solvent and then resuspended in the bisphosphonate containing solution, followed by mixing such as vortexing and/or sonication mixing. In formulations using oiled lecithins, the oiled lecithins are simply combined with the bisphosphonate compounds and mixed by vortexing and/or sonication, if needed.

Another process for making supported bisphosphonate-phospholipid compositions is to form the bisphosphonate-phospholipid mixture, concentrate the mixture, then added the support either in particular form or in sol form. The concentrated mixture is better designed to absorb on the surface of the particular oxide or to be form with a oxide sol into a suitable supported composition.

Suitable oxides include, without limitation, silicas, silicates, aluminas, aluminates, silica-aluminates, aluminum-silicates, magnesium silicates, titanias, magnesias, mixed oxides or mixtures or combination thereof.

Suitable oxide sols include, without limitation, alumina sols, silica sols, magnesia sols or the like or mixture or combination thereof.

Methods for Compounding the Compositions into Oral Medications

The compositions of the present invention can be formulated and presented for oral administration in a variety of formats including, without limitation, granules, pills, tablets, gel coated pills or tablets, gel caps filled with a powder or granule form of the composition, gel caps filled with a fluid form of the composition of this invention, fast dissolving tablets pills or tablets, liquid supplements or the like. For further details on the preparation of pills or tablets, see U.S. Pat. Nos. 6,143,323; 6,200,602; 4,684,632, incorporated herein by reference. For further details on the preparation of capsules for solid and/or fluids (liquid-type forms), see U.S. Pat. Nos. 6,024,980; 5,294,615; 5,073,384; 5,071,643; 4,935,243; 4,894,978; 4,486,412; 4,772,472; 4,708,834 and WO 91/07950, incorporated herein by reference. For further details on the preparation of fast dissolving tablets or pills, see U.S. Pat. Nos. 6,187,336; 6,187,337, incorporated herein by reference.

The compositions of the present invention can also be formulated and/or commutated to a small particle size for dry powder inhalation as is described in U.S. Pat. No. 6,116,237, incorporated herein by reference. The composition of the present invention can also be formulated for nasal delivery systems.

Additives

The composition of the present invention can also include adjuvants including, without limitation, triglycerides, sterols, plant sterols or the like (especially for increasing mobility of the phospholipids) and inert additives or excipients including, without limitation, fillers, binders for making pills or tablets or the like, additive to control pH, stabilizers, or the like. Thus, the present composition can be include neutral lipids or triglycerides to increase phospholipid migration to membrane surfaces such as in the intestinal tract. For further details see U.S. Pat. Nos. 5,955,451; 5,763,422; 5,260,287; 5,260,284; 5,134,129; 5,043,329; 5,032,464; 4,950,658 and 4,918,063, incorporated herein by reference.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

I claim:

1. A pharmaceutical composition for treating osteoporosis consisting essentially of at least one zwitterionic phospholipid and at least one bisphosphonate.

2. The composition of claim 1, wherein the zwitterionic phospholipid is present in an amount sufficient to reduce GI toxicity of the bisphosphonate and the bisphosphonate is present in an amount sufficient to reduce bone resorption.

3. The composition of claim 1, wherein the zwitterionic phospholipid is present in an amount sufficient to reduce GI toxicity of the bisphosphonate and improve bisphosphonate bio-availability when the composition is taken with food and the bisphosphonate is present in an amount sufficient to reduce bone resorption, increase in bone density and/or reduce bone fractures.

4. The composition of claim 3, wherein the amount of bisphosphonate is between about 0.1 mg per dose and about 1000 mg per dose and a ratio of bisphosphonate to zwitterionic phospholipid is between about 1:0.1 and about 1:100.

5. The composition of claim 3, wherein the amount of bisphosphonate is between about 1 mg per dose and about 500 mg per dose and a ratio of bisphosphonate to zwitterionic phospholipid is between about 1:0.5 and about 1:50.

6. The composition of claim 3, wherein the amount of bisphosphonate is between about 2 mg per dose and about 50 mg per dose and a ratio of bisphosphonate to zwitterionic phospholipid is between about 1:1 and about 1:10.

7. The composition of claim 3, wherein the amount of bisphosphonate is between about 2 mg per dose and about 20 mg per dose and a ratio of bisphosphonate to zwitterionic phospholipid is between about 1:1 and about 1:5.

8. The composition of claim 1, wherein the zwitterionic phospholipid is present in an amount sufficient to reduce GI toxicity of the bisphosphonate and the bisphosphonate is present in an amount sufficient to reduce bone resorption, increase in bone density and/or reduce bone fractures.

9. The composition of claim 8, wherein the bisphosphonate is present in an amount between about 0.1 mg per dose and about 1000 mg per dose and a ratio of bisphosphonate to zwitterionic phospholipid is between about 1:0.1 and about 1:100.

10. The composition of claim 8, wherein the bisphosphonate is present in an amount between about 1 mg per dose and about 500 mg per dose and a ratio of bisphosphonate to zwitterionic phospholipid is between about 1:0.5 and about 1:50.

11. The composition of claim 8, wherein the bisphosphonate is present in an amount between about 2 mg per dose and about 50 mg per dose and a ratio of bisphosphonate to zwitterionic phospholipid is between about 1:1 and about 1:10.

12. The composition of claim 8, wherein the bisphosphonate is present in an amount between about 2 mg per dose and about 20 mg per dose and a ratio of bisphosphonate to zwitterionic phospholipid is between about 1:1 and about 1:5.

13. The composition of claim 1, wherein the zwitterionic phospholipid increases the bio-availability of the bisphosphonate from about 2 to about 20 fold.

14. The composition of claim 1, wherein the bisphosphonate is in its zwitterionic form and forms an ionic association complex with the zwitterionic phospholipid.

15. A pharmaceutical composition for treating osteoporosis consisting essentially of at least one zwitterionic phospholipid and at least one bisphosphonate, and a colloidal metal, a metal complex or a mixture or combination thereof.

16. The composition of claim 1, wherein the bisphosphonate is characterized by the general formula (I):

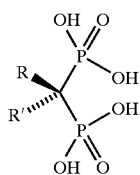

(I)

where R' is H, OH or Cl and R is: (a) an alkyl group having 1 to 6 carbon atoms, optionally substituted with amino, alkylamino, dialkylamino or heterocyclyl, where the alkyl groups in alkylamino and dialkylamino substituents have 1 to 5 carbon atoms and are the same or different in the case of the dialkylamino substituted alkyl groups; (b) a halogen; (c) an arylthio, preferably chlorosubstituted; (d) a cycloalkylamino having 5 to 7 carbon atoms; or (e) a saturated five or six membered nitrogen containing heterocyclyl having 1 or 2 heteroatoms.

17. The composition of claim 1, wherein the phospholipid is characterized by the of general formula (II):

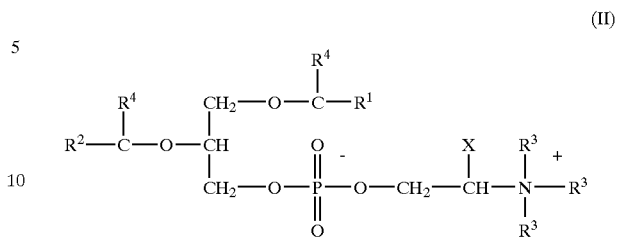

(II)

where $R_1$ and $R_2$ are saturated or unsaturated substitutions ranging from 8 to 32 carbon atoms; $R_3$ is H or $CH_3$, and X is H or COOH; and $R_4$ is $=O$ or $H_2$.

18. The composition of claim 1, wherein the bisphosphonate is selected from the group consisting of 3-amino-1-hydroxypropylidene-1,1-bisphosphonic acid(pamidronate), 4-amino-1-hydroxybutylidene-1,1-bisphosphonic acid (alendronate),N,N-dimethyl-3-amino-1-hydroxypropylidene-1,1-bisphosphonic acid (mildronate, olpadronate), I-hydroxy-3-(N-methyl-N-pentylamino) propylidene-1,(N-methyl-N-pentylamino) propylidene-1,1-bisphosphonic acid (ibandronate), I-hydroxy-2-(3-pyridyl) ethylidene-1,(3-pyridyl) ethylidene-1,1-bisphosphonic acid (risedronate), 1-hydroxyethylidene-1,1-bisphosphonic acid (etidronate), 1-hydroxy-3-(1-pyrrolidinyl) propylidene-1,1-bisphosphonic acid, 1-hydroxy-2-(1-imidazolyl) etylidene-1,1-bisphosphonic(1-imidazolyl) etylidene-1,1-bisphosphonic acid (zoledronate), 1-hydroxy-2-(imidazo[1,2-a]pyridin-3-yl) ethylidene-1,1-bisphosphonic acid (minodronate), 1-(4-chlorophenylthio) methylidene-1,1-bisphosphonic acid (tiludronate), 1-(cycloheptylamino) methylidene-1,1-bisphosphonic acid (cimadronate, incadronate), 6-amino-1-hydroxyhexylidene-1,1-bisphosphonic acid (neridronate) and pharmaceutically acceptable salts thereof and mixtures and combinations thereof.

19. The composition of claim 1, wherein the bisphosphonate is selected from the group consisting of risedronate, alendronate, pamidronate and their pharmaceutically acceptable salts and mixtures and combinations thereof.

20. The composition of claim 1, wherein the zwitterionic phospholipid is selected from the group consisting of phosphatidyl cholines, phosphatidyl ethanolamines, phosphatidylinositol, phosphatidyl serines sphingomyelin or other ceramides, phospholipid containing oils, and mixtures and combination thereof.

21. The composition of claim 1, wherein the zwitterionic phospholipid is selected from the group consisting of phosphatidyl choline (PC), dipalmitoylphosphatidylcholine (DPPC), other disaturated phosphatidyl cholines, lecithin oils and mixture and combinations thereof.

22. A pharmaceutical composition, for treating osteoporosis, consisting essentially of a pharmaceutically effective amount of a bisphosphonate to reduce bone resorption and a sufficient amount of a zwitterionic phospholipid to reduce GI toxicity and increase the bio-availability of the bisphosphonate.

23. The composition of claim 22, the effective amount of the bisphosphonate comprises between about 0.1 mg per dose and about 1000 mg per dose and the sufficient amount of zwitterionic phospholipid is such that a ratio of bisphosphonate to zwitterionic phospholipid is between about 1:0.1 and about 1:100.

24. A pharmaceutical composition for treating osteoporosis consisting essentially of a pharmaceutically effective amount of a bisphosphonate to reduce bone resorption and a sufficient amount of a zwitterionic phospholipid to reduce GI toxicity and increase the bio-availability of the bisphosphonate, and a colloidal metal, a metal complex or a mixture or combination thereof.

25. A pharmaceutical composition consisting essentially of a pharmaceutically effective amount of a bisphosphonate to reduce bone resorption and a sufficient amount of a zwitterionic phospholipid to reduce GI toxicity and increase the bio-availability of the bisphosphonate, where the phospholipid is in its zwitterionic form and the bisphosphonate is in its zwitterionic form combined with a inert carrier.

26. The composition of claim 25, wherein effective amount of the bisphosphonate is between about 0.1 mg per dose and about 1000 mg per dose and the sufficient amount of zwitterionic phospholipid is such that a ratio of bisphosphonate to zwitterionic phospholipid is between about 1:0.1 and about 1:100.

27. A pharmaceutical composition consisting essentially of a pharmaceutically effective amount of a bisphosphonate to reduce bone resorption and a sufficient amount of a zwitterionic phospholipid to reduce GI toxicity and increase the bio-availability of the bisphosphonate, and a colloidal metal, a metal complex or a mixture or combination thereof.

28. The composition of claim 25, wherein the medication is to be taken orally.

29. The medication of claim 25, wherein the medication is to be taken orally with food.

30. An oral medication for treating osteoporosis consisting essentially of a pharmaceutically effective amount a bisphosphonate to reduce bone resorption and an amount of a zwitterionic phospholipid sufficient to reduce GI toxicity and increase the bio-availability of the bisphosphonate combined with an inert carrier and formed into a solid object.

31. The medication of claim 30, wherein the effective amount of the bisphosphonate is between about 0.1 mg per dose and about 1000 mg per dose and the sufficient amount of zwitterionic phospholipid is such that a ratio of bisphosphonate to zwitterionic phospholipid is between about 1:0.1 and about 1:100.

32. An oral medication for treating osteoporosis consisting essentially of a pharmaceutically effective amount a bisphosphonate to reduce bone resorption and an amount of a zwitterionic phospholipid sufficient to reduce GI toxicity and increase the bio-availability of the bisphosphonate, and a colloidal metal, a metal complex or a mixture or combination thereof.

33. A pharmaceutical composition for treating osteoporosis consisting essentially of at least one zwitterionic phospholipid and at least one bisphosphonate, where the phospholipid is in its zwitterionic form and the bisphosphonate is in its zwitterionic form.

34. A pharmaceutical composition, for treating osteoporosis, consisting essentially of a pharmaceutically effective amount of a bisphosphonate to reduce bone resorption and a sufficient amount of a zwitterionic phospholipid to reduce GI toxicity and increase the bio-availability of the bisphosphonate, where the phospholipid is in its zwitterionic form and the bisphosphonate is in its zwitterionic form.

35. An oral medication for treating osteoporosis consisting essentially of a pharmaceutically effective amount a bisphosphonate to reduce bone resorption and an amount of a zwitterionic phospholipid sufficient to reduce GI toxicity and increase the bio-availability of the bisphosphonate combined with an inert carrier and formed into a solid object, where the phospholipid is in its zwitterionic form and the bisphosphonate is in its zwitterionic form.

\* \* \* \* \*